United States Patent [19]
Kistner et al.

[11] Patent Number: 6,139,528
[45] Date of Patent: Oct. 31, 2000

[54] INTRAVENOUS WARMING SYSTEM

[75] Inventors: Thomas L. Kistner, Richardson; Daniel T. Kistner, Van; George C. Burrell, Dallas, all of Tex.

[73] Assignee: Jireh International Corporation, Rockwall, Tex.

[21] Appl. No.: 09/006,635

[22] Filed: Jan. 13, 1998

[51] Int. Cl.[7] .............................. A61F 7/12; A61F 7/00; F28D 7/12
[52] U.S. Cl. .................... 604/114; 607/104; 165/156
[58] Field of Search ...................... 604/113, 114, 604/403, 406, 4; 607/104, 106, 96; 165/156, 102, 142; 422/46

[56] References Cited

U.S. PATENT DOCUMENTS

| | | | |
|---|---|---|---|
| 3,154,663 | 10/1964 | Halvorsen | 604/113 |
| 3,370,153 | 2/1968 | Fresne et al. | |
| 3,443,060 | 5/1969 | Smith | |
| 3,551,641 | 12/1970 | Truhan | |
| 4,231,425 | 11/1980 | Engstrom | 165/156 |
| 4,559,999 | 12/1985 | Servas et al. | 165/156 |
| 5,074,838 | 12/1991 | Krayer | 604/113 |
| 5,106,373 | 4/1992 | Augustine et al. | 604/113 |
| 5,254,094 | 10/1993 | Starkey et al. | 604/113 |
| 5,265,318 | 11/1993 | Shero | 29/447 |
| 5,269,749 | 12/1993 | Koturov | 604/113 |
| 5,514,095 | 5/1996 | Brightbill et al. | 604/113 |
| 5,807,332 | 9/1998 | Augustine et al. | 604/113 |

FOREIGN PATENT DOCUMENTS

WO 87/04887  8/1987  WIPO.

*Primary Examiner*—Sharon Kennedy
*Attorney, Agent, or Firm*—Jones, Day, Reavis & Pogue

[57] ABSTRACT

A system for warming a circulatory fluid is disclosed, which system comprising in a preferred embodiment a warming element consisting of a body defining a bore having irregular fluid flow surfaces and heating elements disposed about said body, a control means electrically coupled to said warming element and a power source.

18 Claims, 3 Drawing Sheets

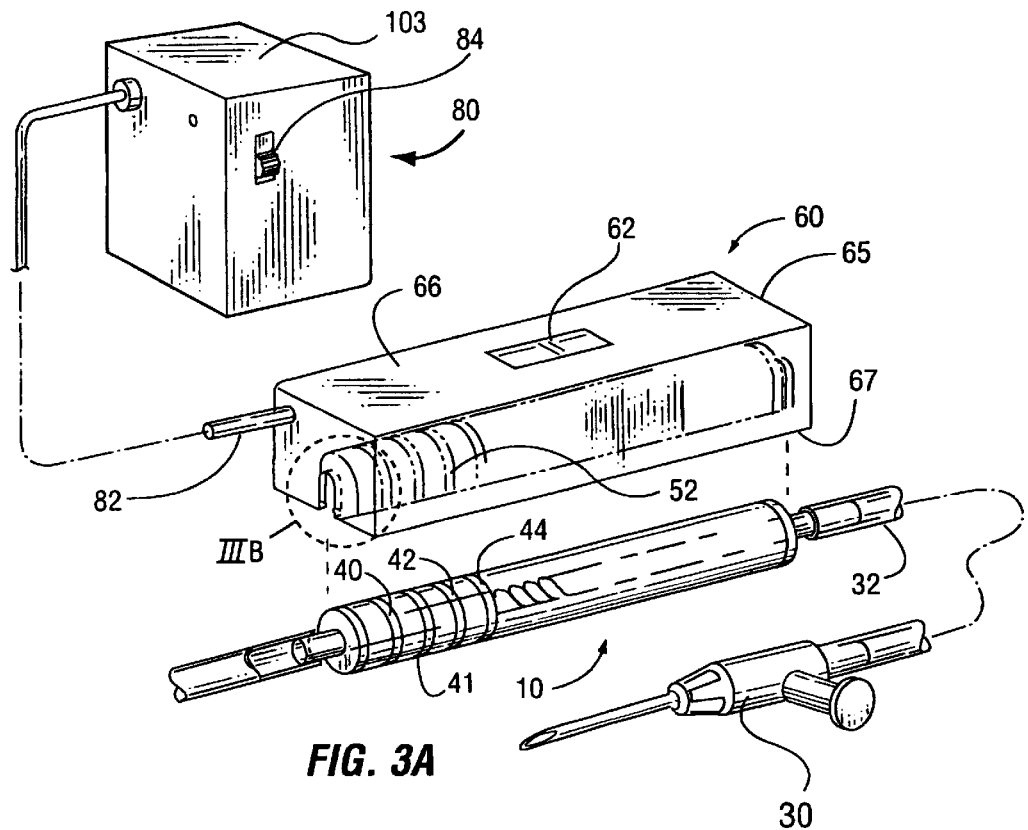
FIG. 3A
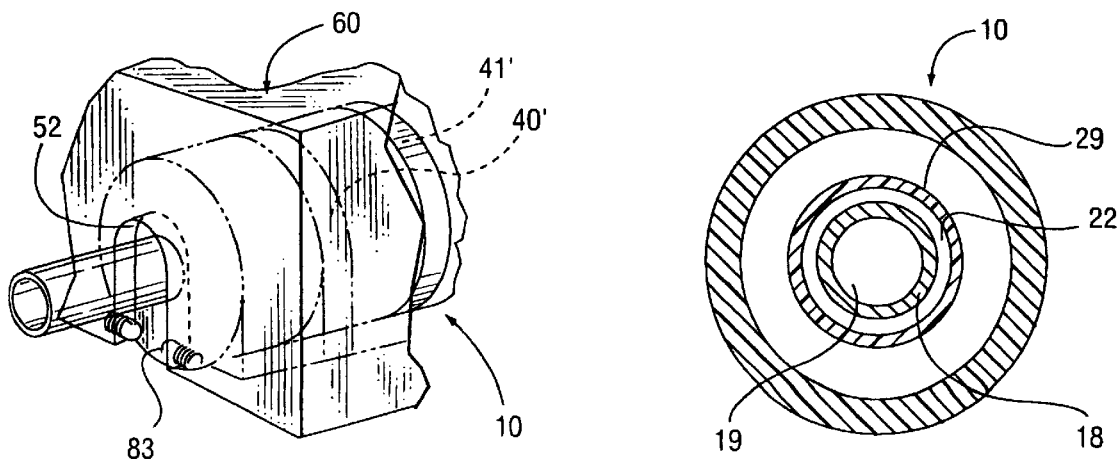
FIG. 3B
FIG. 5

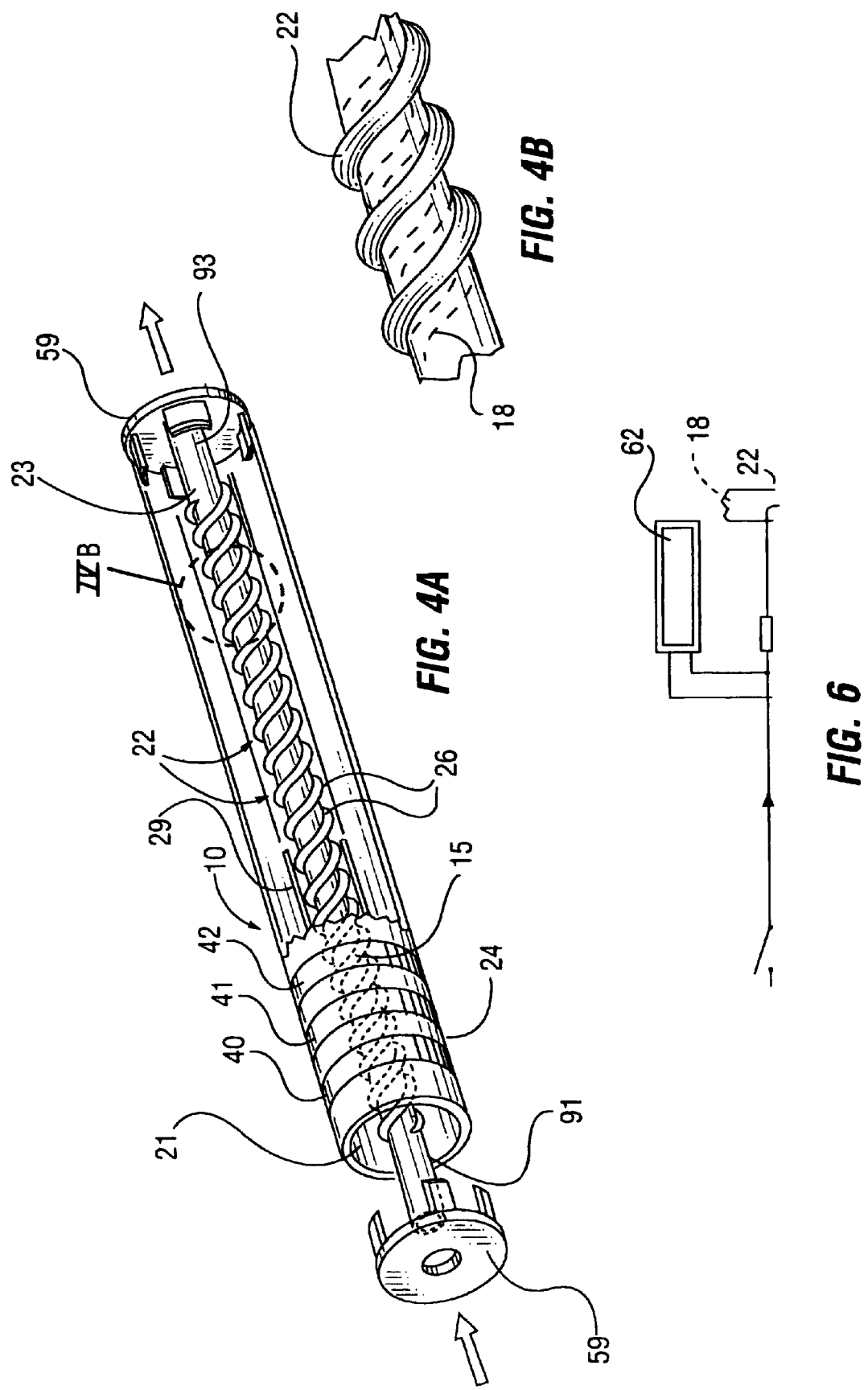

INTRAVENOUS WARMING SYSTEM

BACKGROUND OF THE INVENTION

1. Field of the Invention

The present invention generally relates to an apparatus to warm a liquid to a predetermined temperature. More specifically, the present invention relates to a system to warm a liquid to a desired temperature prior to the introduction of this fluid into the body.

2. Description of the Prior Art

Fluid introduced intravenously should be warmed to a temperature approximating body temperature to prevent the lowering of core body temperatures. Some intravenous fluids are shelf stable and are stored at ambient temperatures which are very often 75° F. or below (more than 20° F. below normal body temperature). Other intravenous fluids must be stored at refrigerated temperatures in the 32° F. to 40° F. range (more than 50° F. below core temperature). In emergency situations, such intravenous fluids may necessarily be introduced at refrigerated temperatures directly into the body through I.V. tubes. Introduction of such liquids at these refrigerated temperatures, however, presents a substantial risk for injurious chill or shock to the body.

A variety of devices have been developed to address the issue of the warming of intravenous fluids. Current systems are generally of two types. Bulk warmers require a significant period of time to warm the product to a desired temperature. Moreover, in order for the bulk warmer to be constantly ready for emergency use, it must be maintained at a proper and set temperature. Such a maintenance procedure, however, is not possible for certain blood products and pharmaceuticals which will degrade if maintained at an elevated temperature.

Moreover, the bulk warmers allow the fluid to cool in the line set as it is administered. This system therefore also experiences drawbacks associated with emergency use since it requires prior anticipation of the need for warmed units as well as the number of units which will ultimately be needed. Furthermore, and assuming the aforereferenced conditions are met, units which are warmed and ready for use must move through several feet of tubing in addition to the drip chamber, thereby offering substantial time and opportunity for such liquids to cool before entering the body.

Previous in-line fluid warmers somewhat address the disadvantages described above except that such in-line systems attempt to warm the fluid in the existing plastic line set which is an inefficient means of heat transfer. Moreover, in-line warming systems are limited in volume, e.g. 30–40 millimeters per minute, and require a 120 volt A/C power source. Additionally, the accuracy of such system is only plus or minus 5 degrees.

SUMMARY OF THE INVENTION

The present invention addresses the above and other disadvantages of prior art systems for warming intravenous fluids.

One preferred embodiment of the invention comprises a system including a heating source, a control unit and a power source. The heating source generally comprises a body in which is formed a bore to carry the fluid in turbulent flow, conductive heating elements disposed about the body and coupled to the power means, where the body and heating elements are disposed in an insulative housing. The control unit is electrically engageable to the heating source to maintain fluids passing through the bore at a predetermined temperature. The control means is also coupled to a power source which may take the form of a battery or direct current source.

The present invention presents a number of advantages over the prior art. One such advantage is the ability to quickly warm an unlimited amount of fluid within a specific temperature range.

Another advantage presented by the invention is the reduction in conductive heat loss by heating the fluid at point of entry into the body.

Another advantage of the present invention is its reads adaption and application to a conventional I.V. line set assembly. In such a fashion, economy of energy is observed while assembly and interconnection may be accomplished in a short amount of time.

Yet another advantage of the present invention lies in its low cost construction thereby enabling a disposable use. In such a fashion, a sterile environment is ensured for each use. Yet another advantage is the adaptability of the present invention to emergency field conditions without loss of time in treatment or transport.

Yet other advantages of the present invention will become obvious after a review of the detailed description of the drawings.

BRIEF DESCRIPTION OF THE DRAWINGS

FIG. 3A illustrates an exploded view of the main elements of one preferred embodiment of the invention.

FIG. 3B is an enlarged portion of the proximal end of the exploded view of the device of FIG. 3A.

FIG. 4A illustrates a perspective view of a warming element of the present invention.

FIG. 4B illustrates a detailed view of the warming element illustrated in FIG. 4A.

FIG. 5 illustrates a cross section of the warming element illustrated in FIG. 4A.

FIG. 6 schematically illustrates the various components of the invention.

DETAILED DESCRIPTION OF THE PREFERRED EMBODIMENTS

Figure 1A:
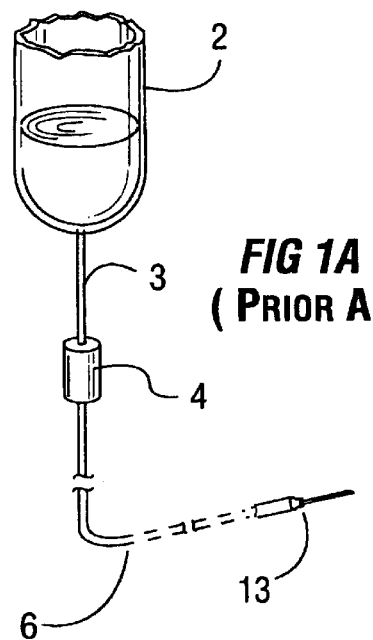
FIG. 1A illustrates elements of a conventional I.V. system.

An illustration of a conventional intravenous setup may be seen by reference to FIG. 1A. As illustrated in FIG. 1A, an intravenous solution, e.g. a saline solution is contained in a bag or bottle 2 which is suspended above the patient in a conventional fashion. Fluid from bag 2 passes by gravity through a conduit or tube 3 into a drip chamber 4, where upon the flow rate is monitored. Fluid passes from chamber 4 through a second conduit 6 which is coupled to a catheter 13 which has been inserted in selected circulatory regions of the body.

The aforedescribed intravenous system has been used from many years for the administration of certain solutions where the temperatures of such solutions could either be maintained at ambient temperature, or the introduction of such solution was a rate slots enough that the lowering of the body core temperature was not deemed to be an issue.

However, other intravenous fluids, e.g. blood products, must be maintained at a refrigerated temperature of 40° F. or less immediately prior to being administered to the patient. Moreover, the flow rate at which such products must be introduced into the body forecloses their use unless or until warmed near body temperature.

Figure 1B:
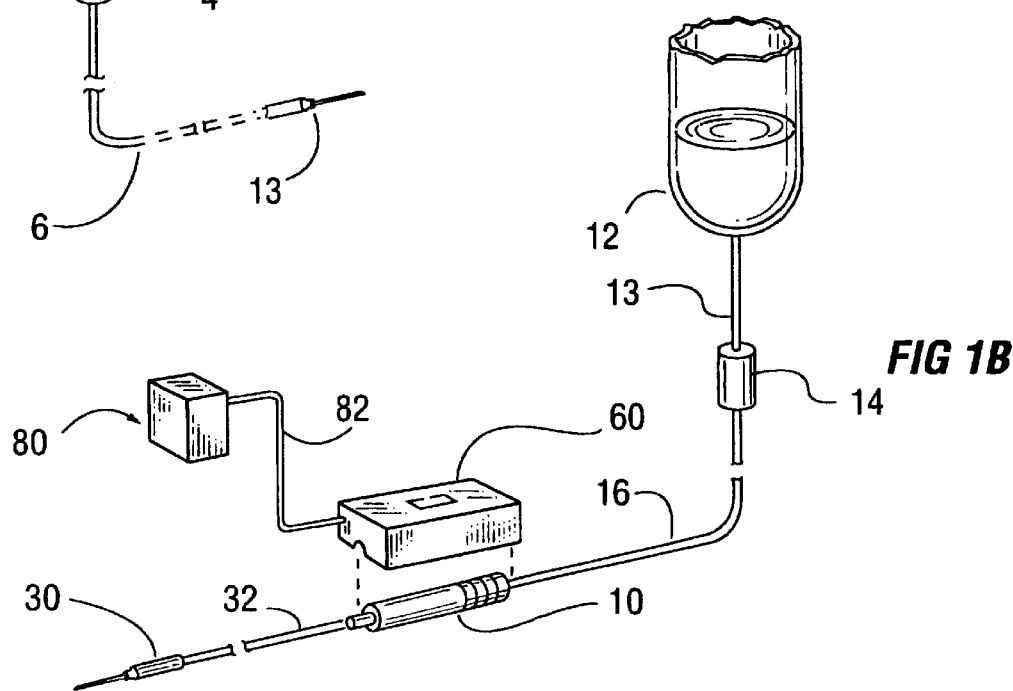
FIG. 1B illustrates one preferred embodiment of various elements of the invention.
Figure 2:
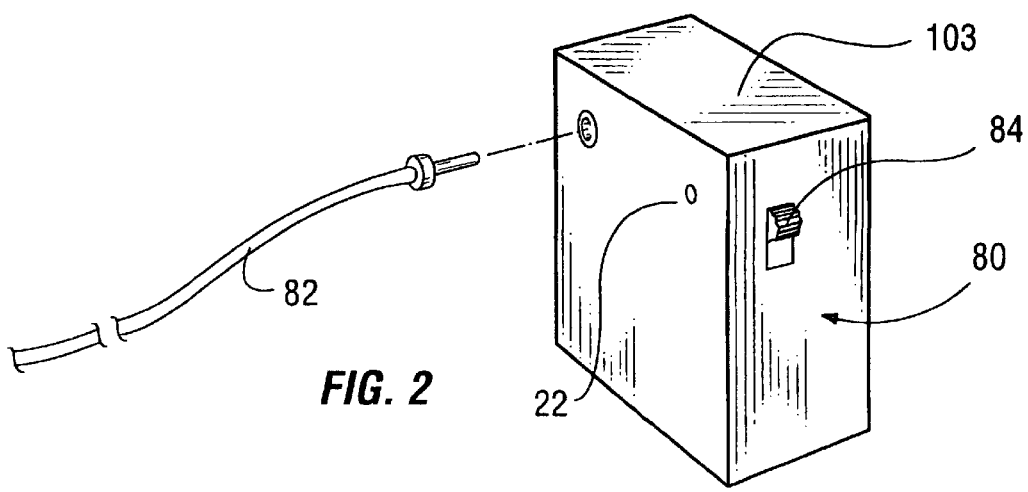
FIG. 2 illustrates a preferred embodiment for a power source applicable with the present invention.

The present invention may be seen by reference to FIGS. 1B–6. FIG. 1B illustrates one preferred embodiment of the present invention as it may be incorporated into the aforedescribed conventional intravenous system in order to warm said solution prior to administration to the patient. By reference to FIG. 1B, fluid from an I.V. bag or bottle 12 passes through a conduit 13 to a drip chamber 14 as described above in conjunction with the conventional intravenous system illustrated in FIG. 1A. Fluid then passes through a second conduit 16 into the system of the present invention which comprises a warming element 10, a control means 60 and a power source 80, as will be discussed in greater detail below. The warmed fluid then passes through a third conduit 32 which is coupled at its terminal end to a catheter 30 which is inserted into the body (not shown).

A preferred embodiment of the warming element 10 of the present invention may be seen by reference to FIGS. 4A–B and 5 where is disclosed a body 18 defining a proximal 21 and a distal 23 end, and a bore 19 formed therethrough. Proximal end 21 includes an elongate terminus 91 receptive to conduit 16 so as to allow fluid communication between bag 12 and bore 19. In such a fashion, distal end 23 also includes an elongate terminus 93 attachable to conduit 32 to allow fluid flow from bore 19 through catheter 30. In a preferred embodiment, conduit 32 is preferably only between 3 and 5 inches in length to avoid conductive heat loss, although other dimensions are also contemplated within the spirit of the invention depending on the given operating environment.

In a preferred embodiment, body 18 is formed of a medical grade stainless steel, e.g. a 316 grade stainless steel. Insulated, resistance type heating elements 22 are disposed around the exterior of body 18 and are electrically coupled to a control means 60 and a power source 80, as will be discussed in greater detail below. (See FIG. 4B). Exemplary heating elements 22 include Nichrome heater wire as made by Watlow Gordon. In a preferred embodiment, elements 22 are wrapped around the exterior of body 18, as will be discussed in greater detail below. In the illustrated embodiment, elements may be encased within an insulative sheath or layer 29.

When coupled to electrical current, elements 22 result in a selective and controlled warming of the walls of body 18. In order to promote greater efficiency in the heat exchange between fluid passing through bore 19, and hence enhance the flow rates achievable through warming element 10, bore 19 is designed to create turbulent fluid flow. In one preferred embodiment, such turbulence is accomplished by use of a bore which defines a multiple helix. The benefit of a helical configuration when translated to the external surface of body 18 is that the groove 26 formed thereby to accommodate heating elements 22, thereby enabling still enhanced heat exchange.

While a helical configuration represents a preferred embodiment, other configuration within bore 19 to create turbulent fluid flow are also contemplated within the spirit of the invention. For example, a bore defining a series of ridges or protrusions (not shown) may also serve to promote heat exchange to the circulatory fluid.

Body 18 and heating elements 22 are preferably contained within a semi rigid insulative member 24. (See FIGS. 4–5). Member 24 may be made of a nylon, though other materials e.g. a closed cell styrofoam, are also contemplated within the spirit of the invention. By reference to FIGS. 3 and 4, member 24 accommodates about its exterior one or more electrical contacts which are annularly disposed about its surface. By reference to FIG. 5, these contacts, designated 40–44, establish electrical contact between control means 60 and warming element 10, when means 60 and warmer 10 are operatively coupled together as will be discussed below. Member 24 is slidably reversible at both ends to caps or closure elements 59, as illustrated.

By reference to FIGS. 3A–B, control means 60 comprises a housing 65 defining at least a top 66 and bottom surface 67, where said top surface 66 defines a groove 52 or slot receivable to element 10. It is contemplated that housing 65 may be made from an injected plastic or other rigid material.

Groove 52 is preferably biased in a "closed" orientation so as to securely hold element 10. In a preferred embodiment, this bias may be accomplished by springs 83 or other resilient elements. Groove 52 includes about its interior one or more electrical contacts 40'–41', which electrically contacts correspond to contacts 40 and 41 on element 10 when element 10 is disposed in said slot 52 as illustrated in FIG. 3B.

In a preferred embodiment, housing 65 defines a surface to accommodate a gauge package which includes temperature indicators 62. These indicators may be analog or digital in nature, though digital is preferred. Indicators 62 are electrically coupled to temperature sensors disposed in or about bore 19.

A temperature sensor (not shown) is disposed at the distal end 23 of element 10, which sensor is coupled to annular contacts 40–44 and is thus readable by indicators 62 when means 60 is electrically coupled to element 10. Sensor may include a bimetal, as made by Watlow Gordon, AF or AJ model, though other configurations are also contemplated within the spirit of the invention.

Control means 60 includes means to ensure that solution passing therethrough is not warmed beyond specific and acceptable temperatures, generally 102° F. Such means include a thermistor (not shown) such as a RM model thermistor manufactured by Watlow Gordon. Thermistor disables the electrical connection between power source 80 and elements 22 if fluid introduced through element 10 exceeds a prescribed maximum temperature. Significantly, the disabling of elements 22 does not impede fluid flow to the patient which will continue, albeit in an ambient, unwarmed state.

Power supply 80 is electrically coupled by means 82 to warming means 10 via control means 60. It is contemplated that power supply may use a rechargeable battery power source, a vehicle/aircraft DC power source, or a standard AC 110/20 power supply. A battery power source is contemplated for use in remote field locations. The power source may include a housing 103 in which are disposed rechargeable batteries, e.g. lithium batteries (not shown), and a switch 84. Alternatively, the power source may include a large cell battery integral with a housing or cover. In the instance of a battery power source, it is desirable to include a conventional low battery indicator. (not shown)

Elements 22 are electrically coupled to power source 80 through control means 60. In one preferred embodiment, elements operate off of 12 volts and draw some 0.5 amps per hour.

A preferred embodiment of the present invention will enable the warming of fluid from a temperature of 50° F. (10° C.) to 100° F. (37.7° C.) at a maximum flow rate of 200 ml/minute. Using battery power, the instant system allows for its use in emergency field conditions and under extreme temperatures.

Although particular detailed embodiments of the apparatus and method have been described herein, it should be understood that the invention is not restricted to the details of the preferred embodiment. Many changes in design, composition, configuration and dimensions are possible without departing from the spirit and scope of the instant invention.

What is claimed is:

1. A warming system for intravenous fluids comprising:
a warming body having a proximal and a distal end, said body defining a bore therethrough to receive and warm an intravenous solution to be introduced into a living body, said bore defining an irregular inner surface to enhance turbulent fluid flow and heat transfer;
heating elements disposed about the exterior of said warming body and electrically coupled to a control means and a power source, where said control means includes circuitry to modify electrical current to said heating elements to maintain temperature in said bore at a desired range;
an insulative housing disposed about said warming body and said heating elements; and
a second housing defining a top and bottom surface, where said bottom surface defines a groove adapted to receive said warming body and said insulated housing.

2. The warming system of claim 1 wherein said bore defines a helical shape about its interior.

3. The warming system of claim 1 wherein said warming body further includes a temperature sensor disposed in said bore and electrically coupled to said control means.

4. The warming system of claim 1 where said insulative housing includes at least one conductive element which is electrically coupled to said heating elements so as to establish electrical contact with a contact element disposed about an interior of said groove of said control means such that electrical contact is established when said insulative housing means is disposed in said groove in said control means.

5. The warming system of claim 1 further including visual temperature indicators, where said indicators are electrical coupled to a temperature sensor disposed in said bore.

6. The warming system of claim 1 and further comprising a catheter and a conduit connected between said catheter and said distal end of said warming body.

7. A warming system for intravenous fluids comprising:
a warming body having a proximal and a distal end, said body defining a bore therethrough to receive and warm an intravenous solution to be introduced into a living body, said bore defining a shape adapted to enhance turbulent fluid flow and heat transfer in fluids introduced therethrough;
heating elements disposed about the exterior of said warming body and electrically coupled to a control means and a power source, where said control means includes circuitry to modify electrical current to said heating elements to maintain temperature in said bore at a desired range;
said warming body and heating elements disposed inside a cylindrical housing and said housing includes at least one insulative layer; and
said housing includes at least one annular contact which is coupled to said temperature sensor and said heating elements, and said contact is adapted to electrically contact complimentary contacts disposed on said control means so as to establish electrical contact between said heating elements and said control means.

8. The apparatus of claim 7 where said warming body further includes a temperature sensor disposed in said bore, where said sensor is operatively coupled to said control means so as to maintain intravenous liquids passing through said bore at a predetermined temperature.

9. The apparatus of claim 8 where said control means includes means coupled to said temperature sensor to interrupt power to said heating elements if said predetermined temperature is exceeded.

10. An electrically powered system for heating an intravenous liquid to a predetermined temperature comprising:
a body having a proximal end and a distal end and defining an irregular bore therethrough to establish turbulent fluid flow of an intravenous liquid to be introduced into a living body;
an electrical resistance heating element disposed about said body such that when electrical current is delivered to said heating element, heat is transferred therefrom to fluid in the bore;
an insulative housing disposed about said body and said heating element;
a second housing defining a top and bottom surface, where said bottom surface defines a groove adapted to receive said body and said insulative housing;
control means electrically coupled to said heating element, said means enabling the maintenance of intravenous liquid flowing through said bore at a predetermined temperature;
a power source coupled electrically to said control means; and
sensor means to monitor the temperature of the intravenous liquid flowing through said bore, where said sensor means is coupled to said control means.

11. The system of claim 10 where said bore defines a series of interlocking helixes.

12. The system of claim 10 where said body is comprised of stainless steel.

13. The system of claim 10 where said body is adapted at its proximal end to be coupled to an intravenous or I.V. supply source and at its distal end to a catheter.

14. The system of claim 10 where said power source includes a battery.

15. The system of claim 10 and further comprising a catheter and a conduit connected between said catheter and said distal end of said body.

16. The warming system of claim 1 wherein said warming body is a readily detachable disposable unit.

17. The warming system of claim 7 wherein said warming body is a readily detachable disposable unit.

18. The electrically powered system of claim 10, wherein said body is a readily detachable disposable unit.

\* \* \* \* \*